United States Patent
Devos et al.

(10) Patent No.: US 10,105,326 B2
(45) Date of Patent: Oct. 23, 2018

(54) PHARMACEUTICAL SOLUTION COMPRISING DOPAMINE FOR USE IN TREATING PARKINSON'S DISEASE

(71) Applicants: CENTRE HOSPITALIER REGIONAL ET UNIVERSITAIRE DE LILLE (CHRU), Lille (FR); UNIVERSITE DE LILLE 2 DROIT ET SANTE, Lille (FR); UNIVERSITE DU LITTORAL COTE D'OPALE, Dunkirk (FR)

(72) Inventors: David Devos, Lille (FR); Caroline Moreau, Lille (FR); Charlotte Laloux, Bourghelles (FR); Jean-christophe Devedjian, Lille (FR)

(73) Assignees: Centre Hospitalier Regional Et Universitaire De Lille (Chru) (FR); Universite De Lille 2 Droit Et Sante (FR); Universite Du Littoral Cote D'Opale (FR)

( * ) Notice: Subject to any disclaimer, the term of this patent is extended or adjusted under 35 U.S.C. 154(b) by 0 days.

(21) Appl. No.: 15/310,364

(22) PCT Filed: May 12, 2015

(86) PCT No.: PCT/EP2015/060511
§ 371 (c)(1),
(2) Date: Nov. 10, 2016

(87) PCT Pub. No.: WO2015/173258
PCT Pub. Date: Nov. 19, 2015

(65) Prior Publication Data
US 2017/0151193 A1 Jun. 1, 2017

(30) Foreign Application Priority Data

May 13, 2014 (FR) .................................. 14 54254
Mar. 9, 2015 (EP) .................................. 15305352

(51) Int. Cl.
| | | |
|---|---|---|
| A61K 31/137 | (2006.01) | |
| A61K 9/08 | (2006.01) | |
| A61P 25/16 | (2006.01) | |
| A61K 9/00 | (2006.01) | |

(52) U.S. Cl.
CPC .......... A61K 31/137 (2013.01); A61K 9/0019 (2013.01)

(58) Field of Classification Search
CPC ........................... A61K 31/137; A61K 9/0019
USPC ....................................................... 514/654
See application file for complete search history.

(56) References Cited

FOREIGN PATENT DOCUMENTS

| | | |
|---|---|---|
| JP | 2008068122 A | 3/2008 |
| MX | 2012012559 A | 4/2014 |
| WO | 03041687 A2 | 5/2003 |

OTHER PUBLICATIONS

Devos et al. Movement Disorders 2009, 24 (7), 993-1000.*
The International Search Report and Written Opinion, dated Aug. 3, 2015, in the corresponding PCT Appl. No. PCT/EP2015/060511.
Chaudhuri KR1, Schapira AH, "Non-motor symptoms of Parkinson's disease: dopaminergic pathophysiology and treatment," Lancet Neurol. 2009;8:464-74.
Devos et al., "Dopa-decarboxylase gene polymorphisms affect the motor response to L-dopa in Parkinson's disease," Parkinsonism Relat Disord. 2014;20:170-5.
Miller et al., "Role of high-affinity dopamine uptake and impulse activity in the appearance of extracellular dopamine in striatum after administration of exogenous L-DOPA: studies in intact and 6-hydroxydopamine-treated rats," J Neurochem. 1999;72:1516-22.
Venton et al., "Real-time decoding of dopamine concentration changes in the caudate-putamen during tonic and phasic firing," J. Neurochem. 2003;87:1284-95.
Olanow et al., "Continuous dopamine-receptor treatment of Parkinson's disease: scientific rationale and clinical implications," Lancet Neurol. 2006;5:677-87.
Pattison et al., "Oxidation of DNA, proteins and lipids by DOPA, protein-bound DOPA, and related catechol(amine)s," Toxicology. 2002;177:23-37.
Fahn and the Parkinson Study Group, "Does levodopa slow or hasten the rate of progression of Parkinson's disease?" J Neurol. 2005;252 Suppl 4:IV37-IV42.
Parkinson Study Group CALM Cohort Investigators, "Long-term effect of initiating pramipexole vs levodopa in early Parkinson disease," Arch Neurol. 2009;66:563-70.
Olanow et al., "Double-Blind, Double-Dummy, Randomized Study of Continuous Intrajejunal Infusion of Levodopa-Carbidopa Intestinal Gel in Advanced Parkinson's Disease," Lancet Neurol. 2014;13:141-9.
Devos D; French Duodopa Study Group, "Patient profile, indications, efficacy and safety of duodenal levodopa infusion in advanced Parkinson's disease," Mov Disord. 2009;24:993-1000.
Manson et al., "Apomorphine monotherapy in the treatment of refractory motor complications of Parkinson's disease: long-term follow-up study of 64 patients," Mov Disord. 2002;17:1235-41.
Drapier et al., "Apomorphine infusion in advanced Parkinson's patients with subthalamic stimulation contraindications," Parkinsonism Relat Disord. 2012;18:40-4.

(Continued)

*Primary Examiner* — Irina Neagu

(57) ABSTRACT

The present invention is directed to pharmaceutical solution comprising at least dopamine for use in treating Parkinson's disease, wherein said pharmaceutical solution is kept under anaerobic conditions from its formulation to its administration.

14 Claims, 4 Drawing Sheets

(56) References Cited

OTHER PUBLICATIONS

Figure 1:
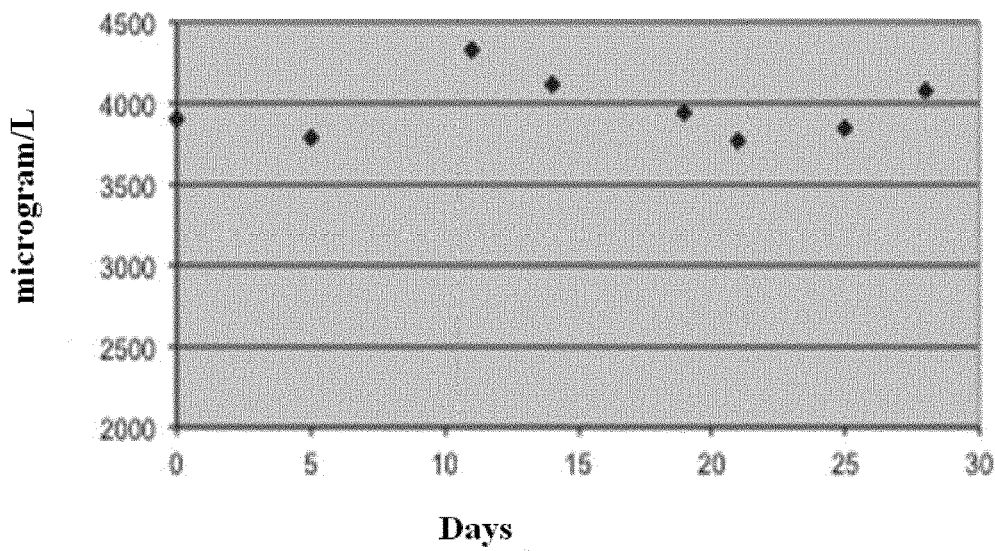
Figure 1:
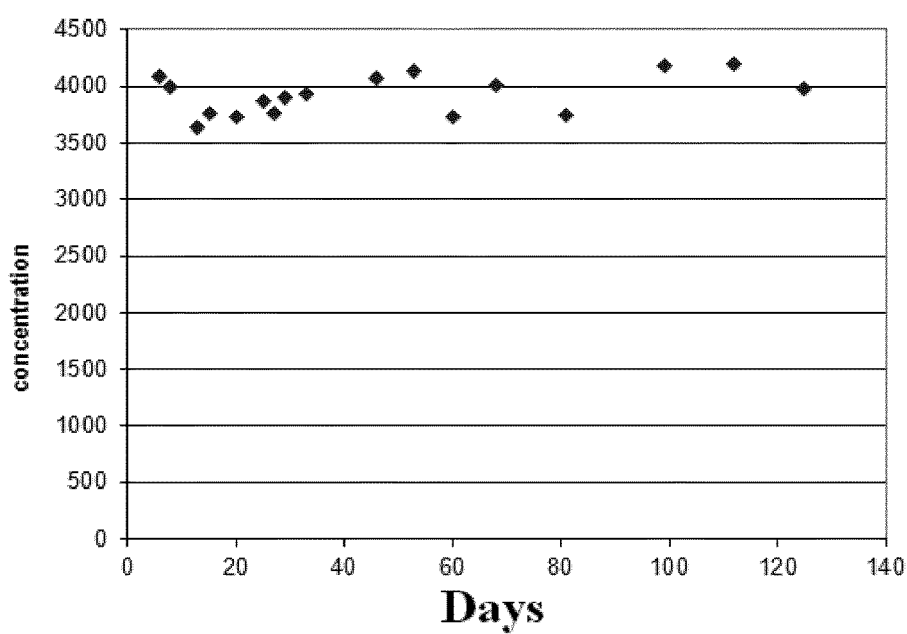

Syed et al., "Ten years' experience with enteral levodopa infusions for motor fluctuations in Parkinson's disease," Mov Disord. 1998;13:336-8.

Rascol et al., "A five-year study of the incidence of dyskinesia in patients with early Parkinson's disease who were treated with ropinirole or levodopa," N Engl J Med. 2000;342:1484-91.

Stocchi et al, "Initiating levodopa/carbidopa therapy with and without entacapone in early Parkinson disease: the STRIDE-PD study," Ann Neurol. 2010;68:18-27.

Sendelbeck et al., "Spatial Distribution of Dopamine, Methotrexate and Antipyrine During Continuous Intracerebral Microperfusion," Brain Research 1985;328:251-258.

De Yebenes et al., "Continuous intracerebroventricular infusion of dopamine and dopamine agonists through a totally implanted drug delivery system in animal models of Parkinson's disease," Mov Disord. 1987;2:143-58.

Akdogan et al., "Hippocampal neuron number loss in rats exposed to ingested sulfite," Toxicol Ind Health. 2011;27:771-8.

Borta et al., "Dopamine and adult neurogenesis," J Neurochem. 2007;100:587-95.

Cenci et al., "Ratings of L-DOPA-induced dyskinesia in the unilateral 6-OHDA lesion model of Parkinson's disease in rats and mice," Curr Protoc Neurosci. Oct. 2007; Chapter 9:Unit 9.25.

Espadas et al., "L-DOPA-induced increase in TH-immunoreactive striatal neurons in parkinsonian mice: insights into regulation and function," Neurobiol Dis. 2012;48:271-81.

Fornai et al., "Time-course and dose-response study on the effects of chronic L-DOPA administration on striatal dopamine levels and dopamine transporter following MPTP toxicity," Brain Res. 2000;887:110-7.

Laloux et al., "Differential susceptibility to the PPAR-γ agonist pioglitazone in 1-methyl-4-phenyl-1,2,3,6-tetrahydropyridine and 6-hydroxydopamine rodent models of Parkinson's disease," Pharmacol Res. 2012;65:514-22.

Hastings et al., "Identification of catechol-protein conjugates in neostriatal slices incubated with [3H]dopamine: impact of ascorbic acid and glutathione," J Neurochem. 1994;63:1126-32.

De Yebenes et al., "Continuous intracerebroventricular infusion of dopamine and dopamine agonists through a totally implanted drug delivery system in animal models of Parkinson's disease," Journal of Neural Transmission (1988) (SUPPL, vol. 27), pp. 141-160.

\* cited by examiner

A

B

A

B

PHARMACEUTICAL SOLUTION COMPRISING DOPAMINE FOR USE IN TREATING PARKINSON'S DISEASE

CROSS-REFERENCE TO RELATED APPLICATIONS

This application is a National Stage Application of PCT/EP2015/060511 filed May 12, 2015, which claims priority from French Patent Application No. 1454254 filed May 13, 2014 and European Patent Application No. 15305352.5 filed on Mar. 9, 2015. Each of the prior mentioned applications is hereby incorporated by reference herein in its entirety.

The present invention relates to a pharmaceutical solution comprising dopamine for use in the treatment of Parkinson's disease, wherein said pharmaceutical solution is kept under anaerobic conditions from its formulation to its administration.

Parkinson's disease (PD) is a progressive neurodegenerative disease affecting the nervous system, in particular the nigro-striatal system comprising dopaminergic neurons. The loss of dopamine in the striatum, as a result of progressive neuronal degeneration in the substantia nigra pars compacta (SNpc), is responsible for motor symptoms.

The pharmacologic treatment of Parkinson's disease can be divided into neuroprotective and symptomatic therapy. Neuroprotective therapy of Parkinson's disease is based on the protection of the dopaminergic neurons in the human substantia nigra and the striatum from the complex degenerative process that causes premature cell death and depletion of dopamine. In practice, however, nearly all of the available treatments are symptomatic in nature and do not appear to slow or reverse the natural course of the disease. Indeed, there is no neuroprotective treatment available on the market at the moment.

Numerous symptomatic treatments have thus focused on the attenuation of this dopamine deficiency (Chauduri et al., 2009; Devos et al. 2013) (1, 2).

As dopamine does not cross the digestive mucosa or the blood brain barrier, its lipophilic precursor L-dopa (Levodopa) has been developed as an orally administered medication in order to alleviate symptoms of Parkinson's disease.

However numerous pharmacokinetic drawbacks are related to the use of L-dopa, and trigger appearance of L-dopa related complications (LDRC). L-dopa has a short half-life in plasma and results in pulsatile dopaminergic stimulation. Under normal conditions, the dopaminergic neurons in the substantia nigra pars compacta (SNpc) fire continuously and the dopamine concentration in the striatum is maintained at a relatively constant level (Miler and Abercrombie, 1999; Venton et al., 2003; Olanow et al., 2006) (3-5). In the dopamine-depleted state, however, intermittent oral doses of levodopa induce discontinuous stimulation of striatal dopamine receptors and after long-term treatment contribute to the dysfunction of the dopaminergic pathways leading to the development of motor complications (Fahn and the Parkinson study group, 2005; Parkinson study group, 2009) (6-7). This oral pulsatile administration leading to alternative periods of underdosage and overdosage could contribute to the worsening of the disease progression (Devos et al., 2013) (2). Indeed intermittent oral administration of L-dopa is unable to restore the continuous nigro-striatal dopaminergic neurotransmission.

Continuous dopaminergic administration might be more physiologic and could prevent high fluctuations in the dopamine level inducing deleterious consequences.

Some treatments have thus focused on a continuous dopaminergic administration. However, direct delivery of a gel of levodopa to the duodenum (Olanow et al, 2014; Devos et al., 2009) (8, 9) or subcutaneous infusions of apomorphine, a dopamine agonist (Manson et al., 2002; Drapier et al., 2012) (10-11), have shown moderate efficiency to reduce LDRC and a poor ergonomy due to external pump (Syed et al., 1998; Devos et al., 2009) (9,12). The use of long-acting dopamine agonists (Rascol et al, 2000) (13), or L-dopa administration with a catechol-O-methyltransferase inhibitor (COMTI) to extend dopamine elimination half-life (Stocchi et al., 2010) (14) failed to significantly improve the severe LDRC.

The spatial distribution of dopamine and methotrexate during continuous intracerebral microperfusion has also been studied (Sendelbeck and Urquhart, 1985) (15). The infusion was made in the brain tissues, more particularly into the mid thalamic region of diencephalon, with an Alzet 2001 mini-osmotic pump filled with dopamine hydrochloride and sodium methotrexate dissolved in deoxygenated artificial cerebrospinal fluid containing sodium fluorescein. The mini-osmotic pump was filled with the solution at least 16 h prior to implantation. However, under these conditions, oxygen will necessarily penetrate into the pump and render the dopamine toxic. Moreover, the study was only made in order to analyze the diffusion of different drugs according to their lipid solubility and polarity, without any therapeutic intention.

The continuous release of dopamine from a mesoporous matrix of $TiO_2$ has been disclosed in MX 2012012559. Dopamine is embedded into the matrix which is produced by a sol gel method. However, said matrix must be implanted into the caudate nucleus of the brain, which implantation being invasive and not convenient at all for the patient. Moreover, this continuous release of dopamine from the mesoporous matrix only enables the symptoms of Parkinson's disease to be controlled, without producing any neuroprotective effect.

Another therapeutic strategy relates to a continuous dopamine infusion directly into the striatum or the lateral ventricle in animals.

Yebenes et al (1987) (16) evaluated the effect of dopamine or dopamine agonists by intracerebroventricular infusion on rats with unilateral lesions of the nigro striatal pathway and MPTP-treated monkeys. The infusion was made in the cerebral lateral ventricle ipsilateral to the lesion with a catheter connected to an Alzet 2001 pump filled with dopamine in different vehicles such as sodium metabisulfite. Sodium metabisulfite was used in order to reduce dopamine's auto-oxidation. It was observed that motor symptoms decreased and that intracerebral concentrations of dopamine increased.

However, contralateral rotation was induced by infusion of dopamine or dopamine agonists with a peak 2 days after the implantation and a slow decrease over a period of 5 days infusion. This effect shows that the continuous infusion induces a tachyphylaxis effect, supported by the reduction in the number of DA-receptors in infused animals. This means that the treatment induces an adaptation phenomenon with a progressive loss of efficiency. It is thus required to progressively increase the dopamine dosage in order to keep a maximal efficiency.

Moreover, a problem of oxidation was observed. Dopamine autoxidation induces formation of quinones and free radicals which are highly cell toxic. This auto-oxidation of dopamine induces oxidation of the surrounding tissue and cell walls. This oxidation has been shown to induce neurotoxicity and consequently could act on the worsening of Parkinson's disease. This problem of auto-oxidation was reduced but remained when dopamine was dissolved in sodium metabisulfite. Moreover, sodium metabisulfite induces tolerance problems such as allergic reaction to sulfites. Besides, a worsening of neuronal degeneration has been shown to be induced by the use of sulfite on pyramidal neurons (Akdogan et al., 2011) (17). This suggests a possible toxicity of sodium metabisulfite in Parkinson's disease model.

Last but not least, the treatment studied in Yebenes et al. was only a symptomatic therapy and was not able to achieve a protection of the dopaminergic neurons in the human substantia nigra and in the striatum.

There is thus still a need in the art for a treatment of Parkinson's disease that does not present the above-mentioned drawbacks. More particularly, there is a need for a composition which allows for a neuroprotective therapy of Parkinson's disease and not only a symptomatic therapy. There is also a need for a composition which is, on the one hand, stable and does not present problems of oxidation leading to increased neurodegeneration of the substantia nigra and related side effects, and, on the other hand, which does not induce tachyphylaxis. Finally, there is a need for a therapeutic composition which does not provide highly invasive and complicated implantation.

The inventors have now found that the above drawbacks can be overcome when dopamine is comprised in a pharmaceutical solution which is kept under anaerobic conditions from its formulation to its administration.

The invention is thus directed to a pharmaceutical solution comprising dopamine for use in the treatment of Parkinson's disease, wherein said pharmaceutical solution is kept under anaerobic conditions from its formulation to its administration."

By "under anaerobic conditions from its formulation to its administration" is meant all necessary conditions for the prevention of oxidation or autoxidation of dopamine until its delivery to the desired site of administration, typically during formulation, conditioning/storage (if any) and administration. This means that the formulation, storage (if any) and use, including the delivery to the desired site of administration, of the pharmaceutical solution of the invention are performed in an environment essentially free or free from oxygen, i.e. containing less than 5% of oxygen, preferably less than 2% of oxygen, more preferably less than 1% of oxygen, more preferably less than 0.5% of oxygen, more preferably about 0% of oxygen. Furthermore, the pharmaceutical solution of the invention by itself is free from oxygen, meaning it contains less than 5% of oxygen, preferably less than 2% of oxygen, more preferably less than 1% of oxygen, more preferably less than 0.5% of oxygen, more preferably about 0% of oxygen.

Indeed, the present invention is based on the unexpected findings that, when dopamine is in a pharmaceutical solution which is kept under anaerobic conditions from its formulation to its administration, it is able to treat Parkinson's disease by efficiently restoring the normal motor activity without inducing tachyphylaxis. Moreover, only slight autooxidation is observed when dopamine is used under anaerobic conditions as described above.

In addition to these symptomatic effects, it has advantageously been found that under these conditions, dopamine efficiently induces neuroplasticity, including at least a neuroprotective effect, to neurons in the striatum and in the SNpc. Such a neuroprotective effect to neurons in the striatum or in the SNpc cannot be induced when dopamine is formulated and/or administered aerobically.

Furthermore, these surprising effects are obtainable when the dopamine is in a pharmaceutical solution which is kept under anaerobic conditions from its formulation to its administration, even without preservative agent. The use of sodium metabisulfite is thus not required and the drawbacks related to this compound are overcome.

The term "neuroplasticity" (or brain plasticity) refers to the brain's ability to reorganize itself by forming new neural connections. In the present invention, neuroplasticity means that the number of neurons is higher when applying the treatment of the invention without treatment for Parkinson's disease is used. Neuroplasticity comprises neuroprotection, neurogenesis (i.e. formation of neurons from stem cells), phenotype change to dopaminergic neurons (i.e. from non-dopaminergic neurons) and/or plasticity changes such as synaptogenesis and dentritogenesis.

The term "neurogenesis" refers to the production of new neurons from stem cells.

It has been previously shown that the proliferation of progenitors is impaired in the subventricular zone (SVZ) and in the subgranular zone (SGZ) of patients affected by Parkinson disease, presumably as a consequence of dopaminergic denervation (Hoglinger et al. 2007) (18). Indeed, experimental depletion of dopamine has been shown to decrease the proliferation of progenitors in both SVZ and SGZ in rodents. In the 6-hydroxydopamine mice model of Parkinson's disease, proliferation in the SVZ was reduced by approximately 40% (Hoglinger et al. 2007) (18).

By "neuroprotective effect" or "neuroprotection" is meant preservation of neuronal structure and/or function of patients affected by Parkinson's disease compared to patients who are not affected by Parkinson's disease. Preferably, it refers to preservation of the number of neurons in the striatum and/or in the substantia nigra pars compacta of patients affected by Parkinson's disease compared to patients who are not affected by Parkinson's disease.

The term "treatment", "treating" and derived terms mean reversing, alleviating, stopping or preventing Parkinson's disease and/or at least one symptom linked to Parkinson's disease. The term "treatment" also refers to a prophylactic treatment which can delay the onset of Parkinson's disease.

The pharmaceutical solution of the invention is pharmaceutically acceptable, i.e. do not produce an adverse, allergic or other untoward reaction when administered to a patient.

By "dopamine" is meant the molecule dopamine in the form of its free base (4-(2-aminoethyl)benzene-1,2-diol) as well as its pharmaceutical acceptable salts, such as e.g. its hydrochloride.

The term "pharmaceutically acceptable salts" refers to any salt obtained from dopamine, said salt having a slightly similar biological activity compared to the biological activity of said compound of the invention. Dopamine is an amine and may form acid addition salts. Suitable acid addition salts are formed from acids which form non-toxic salts. Examples of such acids are hydrochloric acid, hydrobromic acid, sulfuric acid, phosphoric acid, methanesulfonic acid, acetic acid, fumaric acid, succinic acid, lactic acid, citric acid, tartaric acid, and maleic acid, of which hydrochloric acid, hydrobromic acid, sulfuric acid, phosphoric acid, and acetic acid are particularly preferred. Preferably, the pharmaceutically acceptable salt is dopamine hydrochloride.

The pharmaceutical solution of the invention can further comprise complexes, molecules, peptides, salts, vectors or any other compound which can ameliorate or can be beneficial in treatment of Parkinson's disease.

Advantageously, the pharmaceutical solution of the invention is free of preservative agent.

By "preservative agent" is meant all molecules, peptides, salts or other compounds which have an antioxidant effect or which is essential to preserve dopamine and other compounds constituting the pharmaceutical solution of the invention.

In a particularly preferred variant of this embodiment, the pharmaceutical solution of the invention is formulated for a parenteral administration.

Preferably, the pharmaceutical solution contains vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which permit the constitution of injectable solutions upon addition, depending on the case, of sterilized water or physiological saline. For example, when dissolved in saline solution (or solution of sodium chloride) dopamine hydrochloride thus obtained gives a stable acidic solution, having preferably a pH comprised between 4.5 and 7, more preferably between 5.5 and 7, depending on the dilution.

The pharmaceutical solution of the invention is preferably in the form of an aqueous solution.

Regarding the formulation of the dopamine solution, dopamine can be for example directly provided in form of a solution which is administered to the patient. It is also possible to provide solid dopamine, e.g. as powder, which is dissolved in a suitable solvent especially an aqueous solvent to form the solution shortly before administration. Preparing the dopamine solution just or shortly before administration further reduces the risk of oxidation and has the advantage of a longer shelf life of solid dopamine compared to dopamine solutions.

The formulation of the pharmaceutical solution comprising dopamine under anaerobic conditions, i.e. the solution which is free or essentially free from oxygen, can be obtained by any methods known in the art, for example by deoxygenation with inert gas such as nitrogen, freons, argon, xenon, (36)-krypton or neon. To this end, a sparging of an aqueous solution, for example in a salt-bearing aqueous solution, in which dopamine has been previously dissolved can be performed in inert atmosphere as described in FR0114796.

The form (especially the concentration) of the pharmaceutical solution, the route of administration, the dosage and the regimen naturally depend upon the severity of the illness, the age, weight, and sex of the patient, etc.

The pharmaceutical solution of the present invention may be used for the treatment of any living organism, more especially a mammal and more particularly a human and more particularly a human over 45 years old, more preferably over 65 years old.

Advantageously, said pharmaceutical solution is suitable for brain intraventricular administration. More specifically, said pharmaceutical solution is adapted to be administered into the right lateral ventricle, preferably close to the interventricular foramen so that the pharmaceutical solution can be administered into the third ventricle.

Indeed, the present inventors have surprisingly discovered that an administration close to the interventricular foramen, in particular by placing the catheter into right lateral ventricle close to the interventricular foramen, enables the pharmaceutical solution to be directly administered into the third ventricle and allows the bilateral concentration of dopamine into the striatum through the ventricle walls and the subventricular area (SVZ). This administration considerably reduces motor complications, whereas dopamine is laterally concentrated into frontal region and caudate nucleus when administered into the frontal region of the brain, which would be less advantageous with respect to motor complications and development of psychoses.

Hence, the present invention also provides a pharmaceutical solution as described above, wherein said pharmaceutical solution is adapted to be administered into a brain ventricle, preferably into the right lateral ventricle, preferably close to the interventricular foramen.

To this end and in order to perform the administration under anaerobic conditions, the pharmaceutical acceptable solution according to the invention is adapted to be administered with an anaerobical pump.

The administration of the solution of the invention under anaerobic conditions can also be performed by any other method known by the person skilled in the art.

By "anaerobical pump" is meant any device which enables a controlled release of the solution of the invention and which do not degrade the anaerobia of said solution by exposing it to oxygen. Typically, said pump must be compatible with the present invention, and is in particular able to anaerobically deliver a dopamine solution to the desired site of administration.

For example, a SYNCHROMED II pump (commercialized by Medtronic), a IPRECIO pump (commercialized by Iprecio) or an ALZET pump (commercialized by Alzet) can be used for this purpose. The SYNCHROMED II pump (commercialized by Medtronic) is suitable for humans and can thus be preferably used on a human patient. This pump allows complete anaerobic conditions and an excellent stability of the dopamine. Indeed, the inventors have shown that dopamine in anaerobic conditions was stable for at least one month.

Hence, the use of these pumps extremely reduces the risk of oxidation or auto-oxidation of dopamine. The benefit/risk balance for the use of dopamine in the treatment of Parkinson's disease was negative before the development of these anaerobical pumps.

The doses used for the administration can be adapted as a function of various parameters, and in particular as a function of the mode of administration used, of the relevant pathology, or alternatively of the desired duration of treatment.

The present invention also provides a pharmaceutical solution and its use as described above, wherein said pharmaceutical solution is continuously administered with dose variations. Preferably, said pharmaceutical solution is administered with a predominant diurnal dose or with an exclusive diurnal dose.

Indeed, the present inventors have discovered that this administration protocol reduces, and even avoids, tachyphylaxis and allows a long-term efficiency of the treatment without increasing the risk of psychoses' development induced by an excessive nocturnal dose.

Said administration protocol can be easily carried out by using an anaerobical pump as described above, for example a SYNCHROMED II pump. By "continuously administered" is meant an administration of the pharmaceutical solution of the invention on a continuous period, either the entire day and night, i.e. during 24 hours, or only during few hours.

"Predominant diurnal dose" means that the nocturnal dose is lower than the diurnal dose, preferably at least 25% lower than the diurnal dose, more preferably at least 50% lower than the diurnal dose, more preferably at least 70% lower than the diurnal dose, more preferably at least 80% lower than the diurnal dose, more preferably at least 90% lower than the diurnal dose.

By "an exclusive diurnal dose" is meant that there is no nocturnal dose.

In a particular embodiment, the pharmaceutical solution as described above is administered with the following dosage regimen:
 a continuous and stable diurnal dose,
 a bolus administered on morning, and
 optionally, at least a bolus when required, and/or
 optionally, a continuous and stable nocturnal dose lower than the diurnal dose, preferably at least 25% lower than the diurnal dose, more preferably at least 50% lower than the diurnal dose, more preferably at least 70% lower than the diurnal dose, more preferably at least 80% lower than the diurnal dose, more preferably at least 90% lower than the diurnal dose.

By "bolus" is meant a single, relatively large dose of the pharmaceutical solution of the invention that is administered in order to achieve an immediate effect. Preferably, the bolus is in the same way as above described. A bolus is administered on morning and optionally when required, i.e. when the patient is in need of an immediate effect of the treatment.

The inventors have discovered that this administration protocol allows the determination of a minimal efficient dose which can vary from one patient to another. Motor and non-motor symptoms of Parkinson's disease are treated without any of the side effects (dyskinesias, fluctuations, psychosis . . . ), which usually occur with peripheral administration of dopaminergic treatments (i.e oral pulsatile administration of L-dopa, subcutaneous administration of apomorphine, jejunal administration of a L-dopa gel) and autoxidation's risks observed with central (intracerebroventricular) administration of aerobic dopamine. These complications or side effects can be stopped or even prevented if the treatment with anaerobic dopamine according to the invention is administrated before the occurrence of such complications. Furthermore, the use of this minimal efficient dose produces at least neuroprotection, and eventually even neurorestoration. Typically, the use of an anaerobical pump allows determining a minimal efficient dose which is adapted to each case.

By a "minimal efficient dose" is meant a sufficient amount to be effective, at a reasonable benefit/risk ratio applicable to any medical treatment. It will be understood, however, that the total daily usage will be decided by the attending physician within the scope of sound medical judgment. The specific minimal efficient dose for any particular patient in need thereof will depend upon a variety of factors including the age, body weight, general health, sex and diet of the patient, the time of administration, route of administration, the duration of the treatment; drugs used in combination or coincidental with the and like factors well known in the medical arts. For example, it is well known within the skill of the art to start doses of the compound at levels lower than those required to achieve the desired therapeutic effect and to gradually increase the dosage until the desired effect is achieved. The doses can also vary according to the dopa-sensitivity of the patient. For example, it has previously been observed a ratio from 1/100 to 1/300 between the required dose administrated per os and the dose administrated with an intracerebroventricular (ICV) route (e.g. morphine, baclofene).

Also provided herein is a method for treatment of Parkinson's disease comprising administering dopamine to a patient in need thereof, wherein dopamine is formulated, conditioned and administered anaerobically.

FIGURES

FIG. 1: Stability of the solution of the invention over time in anaerobical pumps (A: SYNCHROMED II, B: ALZET 2001)

Figure 2:
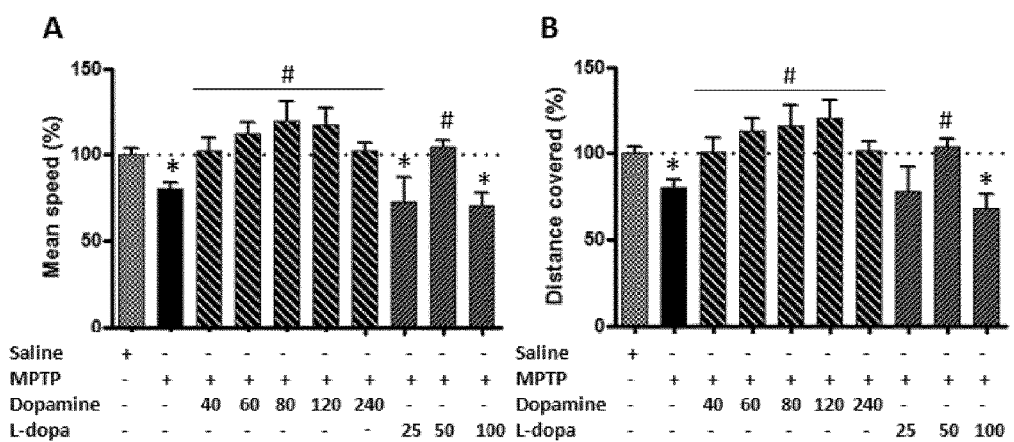

FIG. 2: Restoration of motor deficit in MPTP mice after 7 days of intracerebroventricular dopamine infusion or oral L-dopa treatment. Doses of dopamine are expressed in µg/day and L-dopa in mg/kg/day. Data are expressed in percentage means±SEM from saline mice (n=8-15). *vs. saline mice, # vs. untreated MPTP mice, p<0.05 (one-way ANOVA and LSD Fisher post-hoc tests).
 A: mean speed
 B: distance covered in arena over 10 min.

Figure 3:
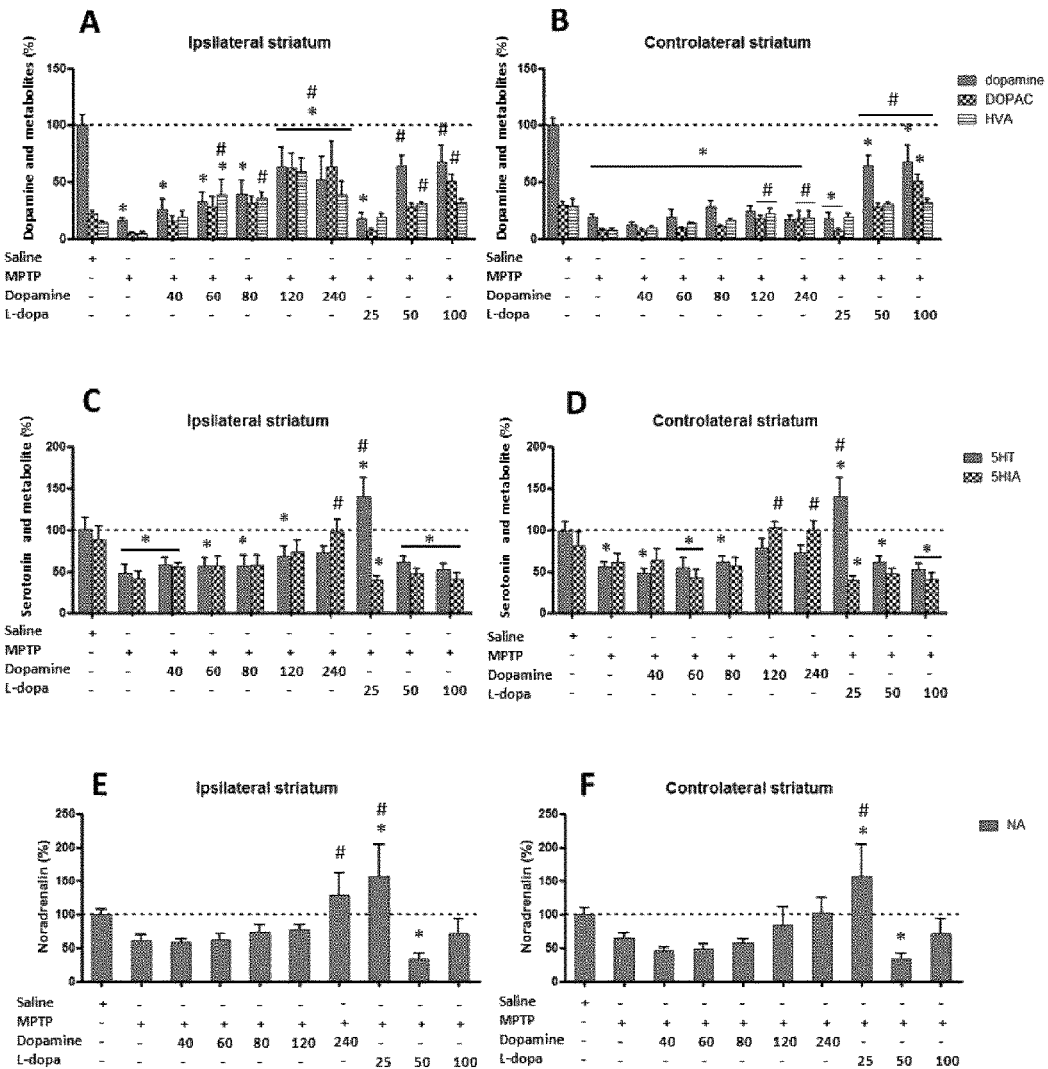

FIG. 3: Modifications of neurotransmitter content in striatum of MPTP mice after 7 days of intracerebroventricular dopamine infusion or oral L-dopa treatment. Dopamine, dihydrophenyl acetate (DOPAC) and homovanillic acid (HVA) (A,B), Serotonin (5HT) and hydroxyindol acetaldehyde (SHIA) (C,D) and Noradrenalin (NA) (E,F) in ipsilateral striatum to the pump infusion of dopamine (A,C,E) and controlateral striatum (B,D,F). Doses of dopamine treatment are expressed in µg/day and L-dopa in mg/kg/day. Data are expressed in percentage means±SEM from saline mice (n=8). *vs. saline mice, # vs. untreated MPTP mice, p<0.05 (one-way ANOVA and LSD Fisher post-hoc tests).

Figure 4:
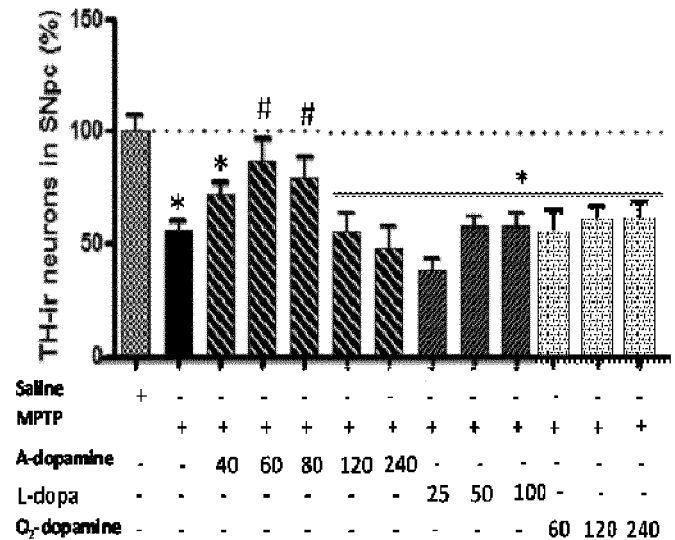
Figure 4:
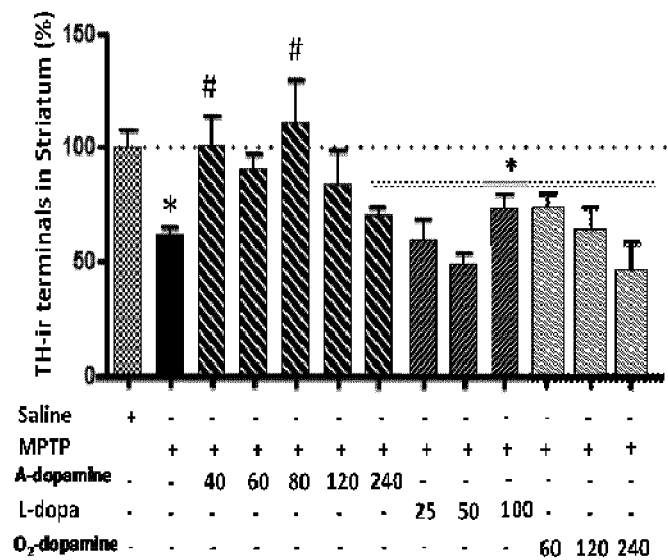

FIG. 4: Restoration of TH-ir staining in SNpc and Striatum of MPTP mice after 7 days of intracerebroventricular dopamine infusion of dopamine prepared and administrated in anaerobic condition, dopamine prepared and administrated in aerobic condition, or with oral L-dopa treatment. Doses of dopamine are expressed in µg/day and L-dopa in mg/kg/day. Data are expressed in percentage means±SD from saline mice (n=10). "A-dopamine" means dopamine prepared and administrated in anaerobic condition, "$O_2$-dopamine" means dopamine prepared and administrated in aerobic condition. *means significant difference between the designated condition and the saline condition. # means significant difference between the designated condition and the MPTP condition. p<0.05 (one-way ANOVA and LSD Fisher post-hoc tests).
 A: TH-ir neurons counting in SNpc
 B: TH-ir optical density in dorsal striatum

EXAMPLES

Example 1

The applicant executed its invention by using MPTP mice. These mice were intoxicated with MPTP in order to reproduce same motor complications as those induced by Parkinson's disease. MPTP is a neurotoxin (1-methyl-4-phenyl-1,2,3,6-tetrahydropyridine) which causes permanent symptoms of Parkinson's disease by destroying dopaminergic neurons in the substantia nigra of the brain.

Different solutions of the invention were produced and infused into cerebral ventricles by using a cannula and a ALZET pump in which a previous deoxygenation with inert gas had been made.

Said solutions have been performed by diluting dopamine hydrochloride in saline which had previously been deoxygenated by nitrogen flushing in inert gas. Said solutions have a pH comprised between 5.58 and 6.84 depending on the dilution. This pH allows the solution to be quite stable as dopamine is in its protonated form as shown at FIG. 1.

MPTP mice get their "normal" motor functions from 0.06 mg/day of dopamine (MPTP DA 0.06) after 7 days of treatment. At the opposite, control mice (MPTP LD) which were treated with high doses of L-Dopa had abnormal behaviors such as dyskinesia as shown at FIG. 2.

The "ventricular walls" of the mice groups have been analyzed. Ventricle's walls of mice treated with high doses of aerobic dopamine comprise numerous black zones unlike ventricle's walls of mice treated with the solution of the invention.

Black color is due to ventricle's walls oxidation of dopamine's quinone and free radicals produced by dopamine's oxidation.

Finally, the inventors discovered that the use of a solution of the invention produce a neuroprotective effect on dopaminergic neurons of substantia nigra, as shown at FIG. 4.

Hence here is proposed a solution for use in treating Parkinson's disease, wherein said solution is administered with doses' variations by infusion into right lateral ventricle, preferably close to the interventricular foramen so that the solution can be administered directly into the third ventricle. The invention allows the obtaining of a higher balance benefit/risk than previous known treatments.

Example 2

Materials and Methods
MPTP-Mice Model and Experimental Design

Animals were group-housed (10 per cage) in a temperature-controlled room (22±2° C.) with a 12/12-hour light/dark cycle. Food and water were freely available in the home cage. A habituation period of 7 days after transportation was respected before any manipulation of the animals.

Five-month-old male C57Bl/6J mice (Elevage Janvier, Le Genest St Isle, France) weighing 28-30 g were used. The mice received four intraperitoneal injections (with 2 h intervals) of saline solution containing 0 ("Saline mice") or 20 mg/kg of MPTP ("MPTP mice") (Sigma Aldrich, St Louis, Mo. USA). Saline or MPTP were administrated at day 0 (D0), the central continuous dopamine infusion or peripheral L-dopa treatment were delivered from $7^{th}$ to the $14^{th}$ day (D7 to D14), and then spontaneous locomotor measurement and sacrifice were performed at D14.

Treatments
Thirteen different groups were set up:
Saline non-implanted mice (treated with saline)
MPTP non-implanted mice (treated with saline)
MPTP implanted with pump filled in anaerobic condition with Dopamine 40 μg/day
MPTP implanted with pump filled in anaerobic condition with Dopamine 60 μg/day
MPTP implanted with pump filled in anaerobic condition with Dopamine 80 μg/day
MPTP implanted with pump filled in anaerobic condition with Dopamine 120 μg/day
MPTP implanted with pump filled in anaerobic condition with Dopamine 240 μg/day.
MPTP implanted with pump filled in aerobic condition with Dopamine 60 μg/day
MPTP implanted with pump filled in aerobic condition with Dopamine 120 μg/day
MPTP implanted with pump filled in aerobic condition with Dopamine 240 μg/day
MPTP mice treated with L-dopa 12.5 mpk+benzeraside 12 mpk, i.p. twice a day
MPTP mice treated with L-dopa 25 mpk+benzeraside 12 mpk, i.p. twice a day
MPTP mice treated with L-dopa 50 mpk+benzeraside 12 mpk, i.p. twice a day Treatment with a Solution of the Invention Solutions of the invention have been prepared by diluting dopamine hydrochloride (sometimes shortly called "dopamine" hereafter) (reference H8502, Sigma-Aldrich) in saline (0.9% NaCl) which had previously been deoxygenated by nitrogen flushing in inert gas. Said solutions have a pH comprised between 5.58 and 6.84 depending on the dilution. This pH allows the solution to be quite stable as dopamine is in its protonated form.

The stability of this drug in ALZET 2001 osmotic pump was tested over 30 days at 37° C. using HPLC assay of dopamine every 4 days (see FIG. 1B). The ALZET 2001 osmotic pump was calibrated to infuse at a rate of 1 μl/hour over 7 days.

Dopamine solution was injected to the pump connected to a brain infusion cannula either in aerobic or in anaerobic condition. Anaerobic experiments were processed in an atmosphere that contained hydrogen 5%, nitrogen dioxide 5% and nitrogen 90% (Bactron anaerobic/environmental chamber, Anaerobe System). If oxygen appeared it was directly combined with hydrogen to give water collected in a bottle. Moreover, Resazurin was added in the area as a redox indicator changing its color in presence of oxygen. Then pumps were maintained in this condition for priming over 4 hours at 37° C. before stereotaxic surgery.

Treatment with L-DOPA

L-DOPA (L-3,4-dihydroxyphenylalanine) was co-administered with a peripheral DOPA decarboxylase inhibitor to prevent the peripheral synthesis of dopamine from L-DOPA. L-dopa methyl ester hydrochloride (Sigma-aldrich) was dissolved in saline with Benserazide 12 mg/kg whatever the L-dopa dose (Cenci and Lundblad, 2007) (19) and was prepared extemporaneously before each injection. L-dopa was administrated intraperitoneally (i.p.) twice a day over 7 days at doses previously described (Espadas et al., 2012; Fornai et al., 2000; Cenci and Lundblad, 2007) (19,21).

ALZET Pump Preparation

The pump chosen for the present study was the 2001 type with 200 μl reservoir volume, allowed to infuse 1μ 1 per hour during 7 days. The brain infusion kit provided a brain canula (30 gauge; ID=0.16 mm; OD=0.31 mm; length below pedestal=3 mm) and a canula support adapted to mice. A catheter tubing was included in the kit and can be cut to the needed length to connect the cannula to the flow moderator of the ALZET pump. The catheter, which connects the cannula to the pump, should be 25% longer than the distance between the subcutaneous site of the pump and the location of the cannula, to allow free movement of the animal's head and neck.

In adapted ambient condition, anaerobic glove box enclosure when required in the protocol, the different dopamine solutions were dissolved and the different parts of the brain infusion assembly and the osmotic pump were filled with the dopamine solutions with a syringe and a specific filling tube.

To definitively eliminate the presence of air bubbles and "start-up" the pump, priming is required the prefilled pumps were placed in an anaerobic closed bottle with sterile 0.9% saline at 37° C. for at least four hours. To avoid any mixing of solutions during the priming and oxygen exposition during the surgical implantation, parafilm was used to drape the end of the canula. The pump and brain infusion assembly are now ready for implantation.

It was also controlled that ALZET pump had no negative impact on motor activity performance by comparing the motor activity performance of saline and MPTP mice either non-implanted (NI) or implanted with an Alzet pump filled with saline (Saline).

Alzet Pump Implantation by Surgery

Mice were anesthetized with chloral hydrate (300 mg/kg, Sigma-Aldrich) and placed in a stereotaxic frame. Briefly, after incision of the scalp and cleaning/drying of the skull, a drilling was performed trough the skull at stereotaxic coordinates for right lateral ventricle, B−0.34 mm, L+1 mm (Paxinos and Watson brain atlas). Then the filled Alzet pump was inserted subcutaneously in the back of the mouse and the brain infusion canula fixed to a canula holder adapted to the stereotaxic frame. The canula holder was then placed at the required antero-posterior and lateral stereotaxic coordinates and the canula was slowly brought down through the trepan hole, up to the lateral ventricle. The support canula was then anchored to the skull with acrylic cement. Once the cement embedding is dry, the head of the canula support was gently cut, the scalp was sutured and animals were allowed to recover under a warm lamp until waking. After surgery, daily cares were carried out along the experiment.

Motor Activity Assessment

After 7 days of treatment (i.p. L-dopa or i.c.v dopamine), spontaneous motor activity was recorded in an actimeter (Panlab, Barcelona, Spain) during 10 minutes. The apparatus was a 45×45×35 cm transparent Plexiglas enclosure equipped with two frames of infrared beams. This apparatus allowed horizontal motor activity (distance traveled, speed, movement type) and rearing behavior to be measured based on infrared beams obstructions. Chosen parameters were collected by Actitrack software (Panlab, Barcelona, Spain).

Nigro-Striatal Tyrosine Hydroxylase Staining and Analysis

After 7 days of treatment (i.p. L-dopa or i.c.v dopamine), animals were deeply anaesthetized with sodium pentobarbital and transcardially perfused with 4% paraformaldehyde in 0.1 M phosphate buffer for tissues fixation (pH 7.4). The brains were removed and, after a post-fixation process, were cryoprotected and frozen.

Fourty-micrometer-thick coronal sections were prepared from the striatum and the Substantia nigra pars compacta (SNpc)/ventral tegmental area (VTA) using a cryostat (Leica, Nussloch, Germany). Serial sections were taken from Bregma+0.98 mm to Bregma−0.82 mm for the striatum, and from Bregma−2.92 mm to Bregma−3.42 mm for the SNc/VTA.

Those free-floating coronal sections were used for immunohistochemical analysis. The sections were incubated successively with rabbit polyclonal anti-tyrosine hydroxylase antibody (1:1000, Chemicon International, CA, USA), goat biotinylated-conjugated polyclonal anti-rabbit antibody (1:500, Vectastain elite ABC kit, Vector Laboratories, CA, USA), and horseradish-peroxidase-conjugated avidin/biotin complex (Vectastain elite ABC kit, Vector Laboratories, CA, USA). Sections were then exposed to diaminobenzidine for detection.

The number of TH-ir neurons ("Tyrosine Hydroxylase-Immunoreactive») in the SNpc was assessed by counting TH-ir neurons of the left and right hemisphere in every 4th section of the SNpc of all experimental groups. The Mercator stereology analysis software (Explora Nova, La Rochelle, France) was used to perform unbiased stereological counts of TH-ir neurons. For the unbiased quantification, a line was drawn around the SNpc of each section. The observer was blinded to the experimental groups. Cells were counted with a 40× using a Nikon Eclipse E600 microscope (Tokyo, Japan). Random and systematic counting frames were used. The number of TH-ir neurons in the SNpc was assessed by counting TH-ir neurons of the left and right hemisphere in every 4th section of the SNpc of all experimental groups. As no difference between left and right SNps was found, TH-ir counted neurons of both sides were pooled and for each animal, a sum of neurons counted in each section was calculated. For the dorsal striatum, TH staining was evaluated as an optical density in each slices, a mean optical density value was calculated for each animal.

High Performance Liquid Chromatography

Fourteen days after MPTP or saline injections for mice or 7 days after pump implantation, animals were deeply anaesthetized with sodium pentobarbital and transcardially perfused with fresh saline. The brains were rapidly removed and dissected to collect left and right striatum, which were immediately frozen in liquid nitrogen. Dopamine, metabolites and 5-cysteinyl-dopamine were determined by HPLC using a Chromsystems 6100 column and Chromsystems mobile-phase by coulometric detection (Coulochem III, ThermoFisher).

Statistical Analysis

All data were expressed as mean±SEM (or SD in table). For all parameters, a one-way ANOVA was used to assess group effect, followed by LSD Fisher post hoc test (STATISTICA 6.1, Statsoft, France). If data did not follow a Gaussian distribution, a Kruskal-Wallis variance analysis was performed, followed by Mann-Whitney post hoc test (STATISTICA 6.1, Statsoft, France). Significance was set at $p<0.05$.

Results

Experiment 1: Determination of Efficiency of Dopamine Infusion on MPTP Mice Motor Deficit (Recorded by Actimetry)

In the experiment here below, the use of the term "dopamine" means "anaerobical dopamine". To assess efficacy of central dopamine infusion (i.e. intracerebro-ventricular dopamine infusion) versus peripheral L-dopa on MPTP mice, symptomatology and locomotor activity measurement was performed after each treatment. As shown at FIG. 2 and as previously reported (Laloux et al, 2012) (22), MPTP mice displayed reduction in mean speed and distance covered in the testing arena.

Seven days of intracerebro-ventricular dopamine infusion restored mean speed and distance covered whatever the five doses tested in MPTP-treated mice. At the opposite, spontaneous locomotor activity in MPTP-treated mice was restored only for 50 mg/kg/day of peripheral L-dopa treatment whereas 25 and 100 mg/day had no effect (FIG. 2).

The motor improvement described in our study demonstrated that dopamine administrated by intraventricular infusion can penetrate the striatum and induce motor improvement in rodent models suffering from Parkinson's disease.

Furthermore, it was observed that the minimal efficient dose of anaerobic dopamine is the dose of 0.06 mg/day, which allowed a significant and complete restoration of the normal motor activity. It was also observed the classical dose-effect of dopamine from 0.04 (with lower efficiency on motor function) to 0.12 mg/day (over dosage on motor function). This perfectly reflects the well-known situation patients having Parkinson's disease. The highest dose of 0.24 mg/day is becoming less efficient as a situation of over dosage.

Last but not least, restoration of the normal motor activity was observed after seven days of intracerebro-ventricular dopamine infusion under anaerobic conditions. On the contrary to previous studies where dopamine was not administered under anaerobic conditions (Yebenes et al.) (16) and in which motor activity decreased after two or three days of treatment (which is a sign of tachyphylaxis), seven days of treatment of the invention does not induce tachyphylaxis.

Experiment 2: Cerebral Dopamine Infusion and L-Dopa Peripheral Treatment Modified Differentially Dopamine, Noradrenalin and Serotonin Contents in Mice Striatum In the experiment here below, the use of the term "dopamine" means "anaerobical dopamine".

After having shown a restoration of motor parameters in MPTP mice treated with the solution of the invention, the neurotransmission modifications induced by both treatments, i.e. solution of the invention and L-Dopa, on the targeted cerebral structure, i.e. dorsal striatum, have been analyzed.

As shown at FIG. 3, MPTP intoxication induced about 85-90% reduction in dopamine (also 70-80% for DOPAC and 60-70% for HVA), 35-50% de noradrenalin and 40-40% serotonin (also 20-50% HIA) content in each striatum.

Cerebral dopamine infusion and L-dopa peripheral treatment induced significant modifications of dopamine, noradrenalin and serotonin striatal contents in MPTP mice.

Furthermore, a parallel dose effect can be observed between the dose of dopamine administrated through the intracerebro-ventricular infusion and the dosage of the dopamine within the striatum. This shows that the dopamine can cross the ventricular barrier and reaches the target zone of the striatum with a logical dose effect. There is a maximum effect reached at 0.12 mg/day. Indeed, increasing the dose to 0.24 mg/day did not allow increasing the dose of dopamine. This is perfectly correlated with the results of motor function measured by actimetry.

In the infused side (ispsilateral striatum), dopamine at 60 and 80 µg/day increased HVA with no effect on DA or DOPAC striatal content and no modification of NA or 5HT neurotransmission systems compared to untreated MPTP mice. Higher doses of dopamine, 120 and 240 µg/day, were able to increase DA and metabolites and the dose of 240 µg/day increased also HIA and NA (FIG. 3, A,C,E).

In the non-infused side (controlateral striatum), dopamine at 60 and 80 µg/day had no effect whereas higher doses increased dopamine and serotonin metabolites (DOPAC, HVA, HIA) with no effect on NA (FIG. 3, B,D,F).

Peripheral injection of 25 mg/day of L-dopa had no effect on dopaminergic neurotransmission but induced an increase in serotonin and noradrenalin in both striatum, overpassing striatal content of control mice, whereas higher doses, i.e. 50 and 100 mg/day, induced a significant increase in dopamine and metabolites in both striatum with no supplemental effect on serotonin and noradrenalin content (FIG. 3C to F).

Surprisingly, peripheral L-dopa and central dopamine had opposite dose-dependent effects. Low doses of L-dopa induced an increase in NA and 5HT and only higher doses were able to modify dopamine, whereas central dopamine infusion induced first an increase of dopamine and the highest doses increased NA and 5HT. Elsewhere, central dopamine induced an increase in dopamine and metabolites whereas L-dopa increases firstly dopamine with few effect on metabolites, suggesting that dopamine induced also an increase in dopamine turnover. L-dopa per os induced a high level of extracellular dopamine with a lower dopamine turnover, suggesting an under use of dopamine and a risk of dopamine toxicity. Conversely, dopamine administered ICV is used with a low level of extracellular dopamine and a lower risk of toxicity related to exogenous administration of dopamine/L-dopa. The toxicity of L-dopa could be also higher regarding the lower level of storage (i.e. lower level of remaining dopaminergic neurons: TH+ neurons).

Experiment 3: Determination of the Impact of Dopamine Infusion on the Nigro-Striatal Pathways Lesions in MPTP Mice.

As shown at FIG. 4, it is first observed that the MPTP model is efficient as MPTP administration resulted in 44.3% loss of TH-expressing neurons in the SNpc compared to saline-injected mice and in 38.2% loss of TH-expressing neurons in the striatum compared to saline-injected mice.

Interestingly, anaerobical dopamine infusion at 60 and 80 µg/day induced a significant increase in TH-ir neurons in SNpc, of respectively 30.65% and 25.19%, compared to MPTP-treated mice whereas L-dopa treatment or aerobical dopamine diffusion (3 h of aerobia) had no significant effect (FIG. 4A). Moreover, if aerobic conditions are maintained for 12 h, a dose of 240 µg/day induces death in all animals.

The observed neuroprotective effect of intracerebro-ventricular anaerobical dopamine infusion was surprising and revealed a great advantage compared to peripheral L-dopa or intracerebro-ventricular aerobical dopamine infusion which were not able to reproduce this effect.

In the striatum, i.c.v. anaerobical dopamine infusion at doses of 40, 60 and 80 µg/day reverse TH-ir terminals loss in MPTP mice whereas oral L-dopa treatment or aerobical dopamine diffusion did not.

Those results provided evidence for a TH-ir recovery after i.c.v. continuous anaerobical dopamine infusion in the striatum but also in the SNpc (depending on the dose administrated), whereas i.c.v. continuous aerobical dopamine infusion or peripheral intermittent L-dopa did not. This functional recovery can be representative of different phenomenon, either synaptic sprouting from surviving dopaminergic neurons or local cells switching toward a dopaminergic phenotype or newly recruited cells from a neurogenesis niche.

It was thus demonstrated that a significantly higher number of dopaminergic cells was achieved within the substantia nigra with a minimal efficient dose of 60 µg/day of anaerobical dopamine. Interestingly, the dose effect on neuroprotection is correlated with previous results on motor function (see Experiment 1) and dopaminergic nigro-striatal neurotransmission (see Experiment 2).

Finally a good therapeutic index was observed (up to 6 fold the minimal efficient dose) since no worsening of the degeneration was observed. Indeed, the range between the lowest efficient dose and the first toxic dose was wide, since the dose of 240 (6 fold the first efficient dose of 40) was not toxic.

Experiment 4: Evaluation of the Dose-Related Auto-Oxidized Dopamine in the Striatum for the Different Doses (5-Cysteinyl Dopamine)

In the experiment here below, "dopamine" means "anaerobical dopamine"

Even if the TH phenotype of nigro-striatal neurons was not altered, the potential toxic effect of an excess of extracellular dopamine remains. Indeed, L-dopa or dopamine treatment have shown to be toxic for surviving neurons by causing additional oxidative stress due to auto-oxidation products of increased dopamine content and its turnover. Both dopamine and its precursor L-dopa are able to auto-oxidise producing a semiquionone radical and subsequently a more stable quinone which react with free cysteine, glutathione, or cysteine found in protein (Hastings and zigmond, 1994; Pattison et al., 2002) (23,24). The reaction between dopamine quinone and cysteine results in the formation of 5-cysteinyl-dopamine, a stable oxidative metabolite of dopamine which is toxic for cells. This could induce an increase in reactive oxidative species having deleterious consequences on tissus.

Therefore, it was analyzed whether central dopamine infusion induced auto-oxidation of dopamine via the determination of the 5-cysteinyl dopamine derivative concentration on the injected striatum.

The results are shown in table 1 here below.

TABLE 1

5-cysteinyl dopamine concentration in the striatum (Data are expressed in mean ± SEM. Dopamine (DA) doses are expressed in µg/day. Statistical significance was assessed with Kruskall wallis variance analysis and LSD Fisher post-hoc test. The significant threshold was set at $p < 0.05$; * vs. saline; # vs. MPTP).

| Group | Frequency (n = 8) | 5-cysteinyl-dopamine (nmol/mg) |
|---|---|---|
| Saline | 0 | 0 |
| MPTP | 0 | 0 |
| MPTP DA 40 | 1 | 0.23 |
| MPTP DA 60 | 3 | 0.26 ± 0.13 |
| MPTP DA 80 | 5 | 0.18 ± 0.05 |
| MPTP DA 120 | 6 | 0.39 ± 0.14 * |
| MPTP DA 240 | 6 | 0.78 ± 0.15 * |

A slight increase in 5-cysteinyl-dopamine shows a slight increase in dopamine auto-oxidation. However, as previously shown, this slight auto-oxidation did not induce a worsening of the neurodegeneration within the striatum and within the substantia nigra and a neuroprotective effect was even observed.

Coloration of the ventricular walls is a good indicator of the performed oxidation. Oppositely to previous experimentations done with dopamine without anaerobic preparation (Yebenes et al., 1987) (16), the dopamine prepared in anaerobia and prepared with adapted doses induced no or very slight oxidation of the ventricular walls (i.e. black coloration of the wall corresponding to severe oxidation).

Only very slight brown coloration was observed on a very small part of the ventricular wall close to the infusion cannula (see first column of the Table: three mice of eight showed only slight partial brown coloration). This is explained by the slight auto-oxidation of dopamine as demonstrated with the parallel increase in 5-cysteinyl-dopamine.

REFERENCES (1) Chaudhuri K R1, Schapira A H. Non-motor symptoms of Parkinson's disease: dopaminergic pathophysiology and treatment. Lancet Neurol. 2009; 8:464-74.
(2) Devos D, Lejeune S, Cormier-Dequaire F, Tahiri K, Charbonnier-Beaupel F, Rouaix N, Duhamel A, Sablonnière B, Bonnet A M, Bonnet C, Zahr N, Costentin J, Vidailhet M, Corvol J C. Dopa-decarboxylase gene polymorphisms affect the motor response to L-dopa in Parkinson's disease. Parkinsonism Relat Disord. 2014; 20:170-5.
(3) Miller D W, Abercrombie E D.; Role of high-affinity dopamine uptake and impulse activity in the appearance of extracellular dopamine in striatum after administration of exogenous L-DOPA: studies in intact and 6-hydroxy-dopamine-treated rats. J Neurochem. 1999; 72:1516-22.
(4) Venton B J, Zhang H, Garris P A, Phillips P E, Sulzer D, Wightman R M. Real-time decoding of dopamine concentration changes in the caudate-putamen during tonic and phasic firing. J Neurochem. 2003; 87:1284-95.
(5) Olanow C W, Obeso J A, Stocchi F. Continuous dopamine-receptor treatment of Parkinson's disease: scientific rationale and clinical implications. Lancet Neurol. 2006; 5:677-87.
(6) Fahn S; Parkinson Study Group. Does levodopa slow or hasten the rate of progression of Parkinson's disease? J Neurol. 2005; 252 Suppl 4:IV37-IV42.
(7) Parkinson Study Group CALM Cohort Investigators. Long-term effect of initiating pramipexole vs levodopa in early Parkinson disease. Arch Neurol. 2009; 66:563-70.
(8) Olanow C W, Kieburtz K, Odin P, Espay A J, Standaert D G, Fernandez H H, Vanagunas A, Othman A A, Widnell K L, Robieson W Z, Pritchett Y, Chatamra K, Benesh J, Lenz R A, Antonini A; LCIG Horizon Study Group. Continuous intrajejunal infusion of levodopa-carbidopa intestinal gel for patients with advanced Parkinson's disease: a randomised, controlled, double-blind, double-dummy study. Lancet Neurol. 2014; 13:141-9.
(9) Devos D; French DUODOPA Study Group. Patient profile, indications, efficacy and safety of duodenal levodopa infusion in advanced Parkinson's disease. Mov Disord. 2009; 24:993-1000.
(10) Manson A J, Turner K, Lees A J. Apomorphine monotherapy in the treatment of refractory motor complications of Parkinson's disease: long-term follow-up study of 64 patients. Mov Disord. 2002; 17:1235-41.
(11) Drapier S, Gillioz A S, Leray E, Péron J, Rouaud T, Marchand A, Vérin M. Apomorphine infusion in advanced Parkinson's patients with subthalamic stimulation contraindications. Parkinsonism Relat Disord. 2012; 18:40-4.
(12) Syed N, Murphy J, Zimmerman T Jr, Mark M H, Sage J I. Ten years' experience with enteral levodopa infusions for motor fluctuations in Parkinson's disease. Mov Disord. 1998; 13:336-8.
(13) Rascol O, Brooks D J, Korczyn A D, De Deyn P P, Clarke C E, Lang A E. A five-year study of the incidence of dyskinesia in patients with early Parkinson's disease who were treated with ropinirole or levodopa. N Engl J Med. 2000; 342:1484-91.
(14) Stocchi F, Rascol O, Kieburtz K, Poewe W, Jankovic J, Tolosa E, Barone P, Lang A E, Olanow C W. Initiating levodopa/carbidopa therapy with and without entacapone in early Parkinson disease: the STRIDE-PD study. Ann Neurol. 2010; 68:18-27.
(15) Sendelbeck S L and Urquhart J. Spatial Distribution of Dopamine, Methotrexate and Antipyrine During Continuous Intracerebral Microperfusion. Brain Research 1985; 328:251-258
(16) de Yebenes J G1, Fahn S, Lovelle S, Jackson-Lewis V, Jorge P, Mena M A, Reiriz J, Bustos J C, Magariños C, Martinez A. Continuous intracerebroventricular infusion of dopamine and dopamine agonists through a totally implanted drug delivery system in animal models of Parkinson's disease. Mov Disord. 1987; 2:143-58.
(17) Akdogan I, Kocamaz E, Kucukatay V, Yonguc N G, Ozdemir M B, Murk W. Hippocampal neuron number loss in rats exposed to ingested sulfite. Toxicol Ind Health. 2011; 27:771-8.
(18) Borta A, Höglinger G U. Dopamine and adult neurogenesis. J Neurochem. 2007; 100:587-95.
(19) Cenci M A, Lundblad M. Ratings of L-DOPA-induced dyskinesia in the unilateral 6-OHDA lesion model of Parkinson's disease in rats and mice. Curr Protoc Neurosci. 2007 October; Chapter 9: Unit 9.25.

(20) Espadas I, Darmopil S, Vergaño-Vera E, Ortiz O, Oliva I, Vicario-Abejón C, Martín E D, Moratalla R. L-DOPA-induced increase in TH-immunoreactive striatal neurons in parkinsonian mice: insights into regulation and function. Neurobiol Dis. 2012; 48:271-81.

(21) Fornai F, Battaglia G, Gesi M, Giorgi F S, Orzi F, Nicoletti F, Ruggieri S. Time-course and dose-response study on the effects of chronic L-DOPA administration on striatal dopamine levels and dopamine transporter following MPTP toxicity. Brain Res. 2000; 887:110-7.

(22) Laloux C, Petrault M, Lecointe C, Devos D, Bordet R. Differential susceptibility to the PPAR-γ agonist pioglitazone in 1-methyl-4-phenyl-1,2,3,6-tetrahydropyridine and 6-hydroxydopamine rodent models of Parkinson's disease. Pharmacol Res. 2012; 65:514-22.

(23) Hastings T G, Zigmond M J. Identification of catechol-protein conjugates in neostriatal slices incubated with [3H]dopamine: impact of ascorbic acid and glutathione. J Neurochem. 1994; 63:1126-32.

(24) Pattison D I, Dean R T, Davies M J. Oxidation of DNA, proteins and lipids by DOPA, protein-bound DOPA, and related catechol(amine)s. Toxicology. 2002; 177:23-37.

The invention claimed is:

1. A method of treating Parkinson's disease, comprising administering to a patient in need thereof a pharmaceutically effective amount of a pharmaceutical solution comprising dopamine, wherein said pharmaceutical solution is kept under anaerobic conditions from its formulation to its administration, wherein the pharmaceutical solution is free of preservative agent.

2. The method according to claim 1, wherein dopamine is dopamine hydrochloride.

3. The method according to claim 1, wherein said solution is adapted to be administered into a brain ventricle.

4. The method according to claim 1, wherein said solution is adapted to be administered into the right lateral ventricle.

5. The method according to claim 1, wherein said solution is adapted to be administered close to the interventricular foramen.

6. The method according to claim 1, wherein said solution is adapted to be administered with an anaerobical pump.

7. The method according to claim 1, wherein said solution is continuously administered with dose variations.

8. The method according to claim 1, wherein said solution is administered with a predominant diurnal dose or with an exclusive diurnal dose.

9. The method according to claim 1, wherein said solution is administered with the following dosage regimen:
a continuous and stable diurnal dose,
a bolus administered on morning, and
optionally, at least a bolus when required, and/or
optionally, a continuous and stable nocturnal dose lower than the diurnal dose.

10. The method according to claim 9, wherein the continuous and stable nocturnal dose is at least 25% lower than the diurnal dose.

11. The method according to claim 9, wherein the continuous and stable nocturnal dose is at least 50% lower than the diurnal dose.

12. The method according to claim 9, wherein the continuous and stable nocturnal dose is at least 70% lower than the diurnal dose.

13. The method according to claim 9, wherein the continuous and stable nocturnal dose is at least 80% lower than the diurnal dose.

14. The method according to claim 9, wherein the continuous and stable nocturnal dose is at least 90% lower than the diurnal dose.

* * * * *